United States Patent
Butterick, III et al.

(10) Patent No.: US 9,587,187 B2
(45) Date of Patent: Mar. 7, 2017

(54) ALKYL TRITYL PHENYL ETHERS

(71) Applicants: Rohm and Haas Company, Philadelphia, PA (US); Dow Global Technologies LLC, Midland, MI (US)

(72) Inventors: Robert Butterick, III, Swedesboro, NJ (US); George David Green, Cary, IL (US); Raymond J. Swedo, Mount Prospect, IL (US)

(73) Assignees: DOW GLOBAL TECHNOLOGIES LLC, Midland, MI (US); ROHM AND HAAS COMPANY, Philadelphia, PA (US)

( * ) Notice: Subject to any disclaimer, the term of this patent is extended or adjusted under 35 U.S.C. 154(b) by 0 days.

(21) Appl. No.: 14/782,339

(22) PCT Filed: Apr. 4, 2014

(86) PCT No.: PCT/US2014/033004
§ 371 (c)(1),
(2) Date: Oct. 5, 2015

(87) PCT Pub. No.: WO2014/165776
PCT Pub. Date: Oct. 9, 2014

(65) Prior Publication Data
US 2016/0040082 A1   Feb. 11, 2016

Related U.S. Application Data
(60) Provisional application No. 61/808,672, filed on Apr. 5, 2013.

(51) Int. Cl.
| | | |
|---|---|---|
| *C10L 1/18* | (2006.01) | |
| *C10L 1/00* | (2006.01) | |
| *C07C 43/205* | (2006.01) | |
| *C10L 1/183* | (2006.01) | |
| *C10L 1/185* | (2006.01) | |

(52) U.S. Cl.
CPC .......... *C10L 1/003* (2013.01); *C07C 43/205* (2013.01); *C07C 43/2055* (2013.01); *C10L 1/18* (2013.01); *C10L 1/183* (2013.01); *C10L 1/1852* (2013.01); *C10L 2230/16* (2013.01); *C10L 2290/24* (2013.01)

(58) Field of Classification Search
CPC ........ C10L 1/003; C10L 1/183; C10L 1/1852; C10L 1/18; C10L 2230/16; C10L 2290/24; C07C 43/205; C07C 43/2055
See application file for complete search history.

(56) References Cited

U.S. PATENT DOCUMENTS

| | | | |
|---|---|---|---|
| 1,873,290 A | 8/1932 | Coffey et al. | |
| 5,981,283 A | 11/1999 | Anderson, II et al. | |
| 7,858,373 B2 | 12/2010 | Banavali et al. | |
| 2010/0196242 A1 | 8/2010 | Stanic et al. | |
| 2014/0123549 A1 | 5/2014 | Green et al. | |

FOREIGN PATENT DOCUMENTS

| | | | |
|---|---|---|---|
| CN | 101037381 | * | 9/2007 |
| EP | 489492 A1 | | 6/1992 |
| EP | 512404 A1 | | 11/1992 |
| WO | 2012154646 A1 | | 11/2012 |
| WO | 2012154668 A1 | | 11/2012 |
| WO | 2013/116582 A1 | | 8/2013 |
| WO | 2013165839 A1 | | 11/2013 |
| WO | 2014008164 A1 | | 1/2014 |

OTHER PUBLICATIONS

"Index of subjects", J. Chem. Soc. (Resumed), p. 3012 (1929).
Barroeta, et al., "Kinetics and Substituent Effects in Electrophilic Aromatic Substitution. II. Tritylation of Catechol and its Monoether", J. Org. Chem., vol. 31, pp. 2330-2333, (1966).
Chuchani, "Chuchani: Tritylation of ortho-Disubstituted Benzenes", J. Chem. Soc., pp. 1753-1756 (1959).
Chuchani, "Condensation of Chlorotriphenylmethane with ortho-Disubstituted Benzenes. Further Evidence on the Systematic Difference of Activation of ortho- and para- Directing Groups." J. Chem. Soc., pp. 325-326 (1960).
Chuchani, et al., "Kinetics and Substituent Effects in Electrophillic", J. Org. Chem., vol. 31, No. 5, pp. 1573-1576 (1966).
Clapp, "The Aldehydic Constituents from the Ethanolysis of Spruce and Maple Woods", J. Am. Chem. Soc., vol. 61, No. 2, pp. 523-524 (1939).

(Continued)

*Primary Examiner* — Cephia D Toomer
(74) *Attorney, Agent, or Firm* — Kenneth Crimaldi

(57) ABSTRACT

A compound having formula (I)

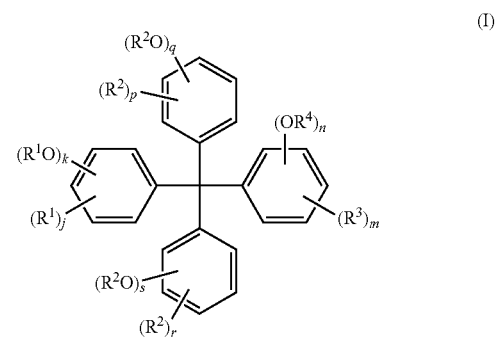

wherein $R^1$ and $R^2$ independently represent $C_1$-$C_6$ alkyl; $R^3$ is $C_1$-$C_6$ alkyl; $R^4$ is $C_1$-$C_{18}$ alkyl or $C_4$-$C_{18}$ heteroalkyl; m is zero, one, two or three; n is one, two or three; and j, k, p, q, r and s independently are zero, one or two; provided that at least one of j, k, p, q, r and s is not zero.

6 Claims, No Drawings

(56) References Cited

OTHER PUBLICATIONS

Cook, et al., "Oxidation of Hindered Phenols. X. Effect of 4-Substituents upon the Behavior of 2,6-Di-t-butylphenoxy Radicals", J. Org. Chem., vol. 25, pp. 1429-1431 (1960).
Iddles, et al., "Rearrangement of the Triphenylmethyl Ether of Ortho Cresol: Direct Synthesis of 3-Methyl-4-methoxyphenyltriphenylmethane", J. Am. Chem. Soc., pp. 2757-2759 (1940).
Llewellyn, et al., "The Condensation of Some Tertiary Aryl Substituted Carbinols with Phenol in the Presence of Aluminum Chloride", J. Am. Chem. Soc., vol. 60, pp. 59-62, (1938).
Nandanwar, et al., "Formation of Ruthenium Nanoparticles by the Mixing of Two Reactive Microemulsions," Ind. Eng. Chem. Res., vol. 50, pp. 1145-1151 (2011).
Schoepfle, et al., "The Reaction between Triarylmethyl Halides and Phenylmagnesium Bromide. II", J. Am. Chem. Soc., vol. 58, pp. 791-794 (1936).
Varin, et al., "Structural stability of sodium borohydride (NaBH4) during controlled mechanical milling," J. Alloys and Compounds, vol. 397 pp. 276-281 (2005).
Shulgin, "The Baeyer-Villiger Condensation. I. ortho-Tritylation of Phenols", J. Org. Chem., vol. 27, pp. 3868-3872 (1962).
Marvel, et al, "Alkyl Substituted Hexaarylethanes. IX.1 Symmetry and Steric Effects as Factors in Dissociation", J. Chem. Soc., pp. 1892-1896, vol. 63 (1941).
White, et. al, "A Determination of the HR Acidity Function for Sulfuric Acid-Aqueous Acetic Acid", J. Org. Chem., vol. 27, pp. 2915-2917 (1962).

* cited by examiner

ALKYL TRITYL PHENYL ETHERS

This invention relates to new compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula (I)

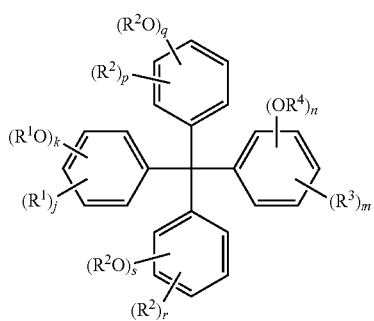

(I)

wherein $R^1$ and $R^2$ independently represent $C_1$-$C_6$ alkyl; $R^3$ is $C_1$-$C_6$ alkyl; $R^4$ is $C_1$-$C_{18}$ alkyl or $C_4$-$C_{18}$ heteroalkyl; m is zero, one, two or three; n is one, two or three; and j, k, p, q, r and s independently are zero, one or two; provided that at least one of j, k, p, q, r and s is not zero.

The present invention further provides a method for marking a petroleum hydrocarbon or a liquid biologically derived fuel; said method comprising adding to said petroleum hydrocarbon or liquid biologically derived fuel at least one compound having formula (I)

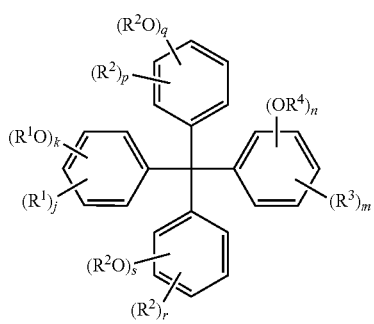

(I)

wherein $R^1$ and $R^2$ independently represent $C_1$-$C_6$ alkyl; $R^3$ is $C_1$-$C_6$ alkyl; $R^4$ is $C_1$-$C_{18}$ alkyl or $C_4$-$C_{18}$ heteroalkyl; m is zero, one, two or three; n is one, two or three; and j, k, p, q, r and s independently are zero, one or two; provided that at least one of j, k, p, q, r and s is not zero; and wherein each compound having formula (I) is present at a level from 0.01 ppm to 20 ppm.

DETAILED DESCRIPTION

Percentages are weight percentages (wt%) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are saturated. Preferably, alkyl groups are unsubstituted. Preferably, alkyl groups are linear or branched. A "heteroalkyl" group is an alkyl group in which one or more methylene groups has been replaced by O or S. Preferably, heteroalkyl groups contain from one to six O or S atoms, preferably from one to four, preferably from one to three. The methylene groups replaced by O or S were bonded to two other carbon atoms in the corresponding alkyl group. Preferably, heteroalkyl groups do not contain S atoms. Heteroalkyl groups may be substituted by OH, SH or $C_1$-$C_{18}$ alkoxy groups, preferably OH or $C_1$-$C_6$ alkoxy groups, preferably hydroxy or $C_1$-$C_4$ alkoxy groups. Examples of heteroalkyl groups include oligomers of ethylene oxide, propylene oxide or butylene oxide having two to six units of the alkylene oxide (preferably two to four, preferably two or three) and a terminal hydroxy or $C_1$-$C_6$ alkoxy group (preferably hydroxy or $C_1$-$C_4$ alkoxy, preferably hydroxy or methoxy, preferably hydroxy); an example of an ethylene oxide oligomer is $—\{(CH_2)_2O\}_iR^2$, where i is an integer from two to six and $R^2$ is hydrogen or $C_1$-$C_6$ alkyl. Preferably, i is from two to four, preferably two or three. Preferably, $R^2$ is hydrogen or $C_1$-$C_4$ alkyl, preferably hydrogen or methyl, preferably hydrogen. Preferably, the compounds of this invention contain elements in their naturally occurring isotopic proportions.

Preferably, $R^1$ and $R^2$ independently are $C_1$-$C_4$ alkyl; preferably methyl or ethyl; preferably methyl. Preferably, $R^1$ and $R^2$ are saturated. $R^1$, $OR^1$, $R^2$ and $OR^2$ may be at any available positions on the benzene rings to which they are attached, preferably the positions meta and para to the quaternary carbon to which all four benzene rings are attached.

Preferably, j, k, p, q, r and s independently are zero or one. Preferably, k, q and s are zero. Preferably, q=s and p=r. Preferably, j is one. Preferably, p and r are one. Preferably, $R^4$ is $C_2$-$C_{12}$ alkyl or $C_4$-$C_{12}$ heteroalkyl, preferably $C_2$-$C_{12}$ alkyl, preferably $C_3$-$C_{12}$ alkyl, preferably $C_4$-$C_{12}$ alkyl, preferably $C_4$-$C_{10}$ alkyl, preferably $C_6$-$C_{10}$ alkyl. Preferably, $R^4$ is saturated. Preferably, $R^4$ is linear or branched, preferably linear. Preferably, $R^3$ is $C_2$-$C_6$ alkyl, preferably $C_3$-$C_6$ alkyl, preferably $C_4$-$C_6$ alkyl, preferably $C_3$-$C_4$ alkyl, preferably sec-butyl, t-butyl or isopropyl. Preferably, $R^3$ is saturated. Preferably, $R^3$ is linear or branched, preferably branched. $R^3$ and $OR^4$ may be at any available position on the benzene ring to which they are attached, preferably the positions meta and para to the quaternary carbon to which all four benzene rings are attached. Preferably, when n is one, $OR^4$ is at the para position. Preferably m is zero, one or two; preferably zero or one. Preferably n is one or two, preferably one. Preferably, m is one and n is one. Preferably, n is two and m is zero. When any of j, k, p, q, r, s, m and n is zero, the associated substituent is absent, e.g., when m is zero, $R^3$ is absent.

In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., J. Pharm. Sci., vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art, e.g., reaction of substituted esters with aryl Grignard reagents and arylation with substituted phenols, followed by alkylation with organic halides in the presence of base. For example, tritylated phenolic ethers may be prepared according to the following reaction scheme, in which, for simplicity, j, p and r are one and k, q and s are zero. All other symbols are as defined above. Products having more complicated substitution patterns can be made from the corresponding starting materials using the same process. In an alternative synthesis, a substituted or unsubstituted benzophenone is allowed to react with a substituted or unsubstituted phenyl Grignard reagent to produce the trityl alkyl phenol, which then reacts with R4X.

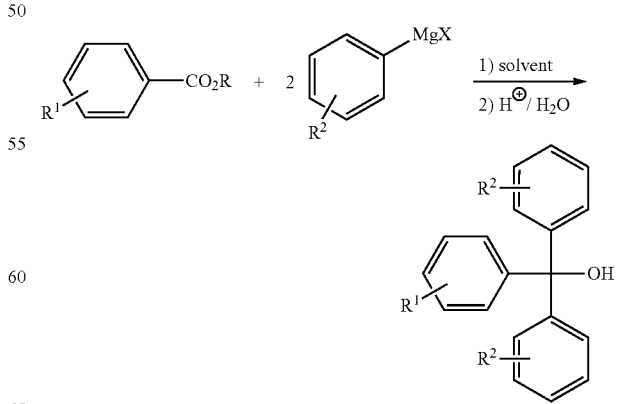

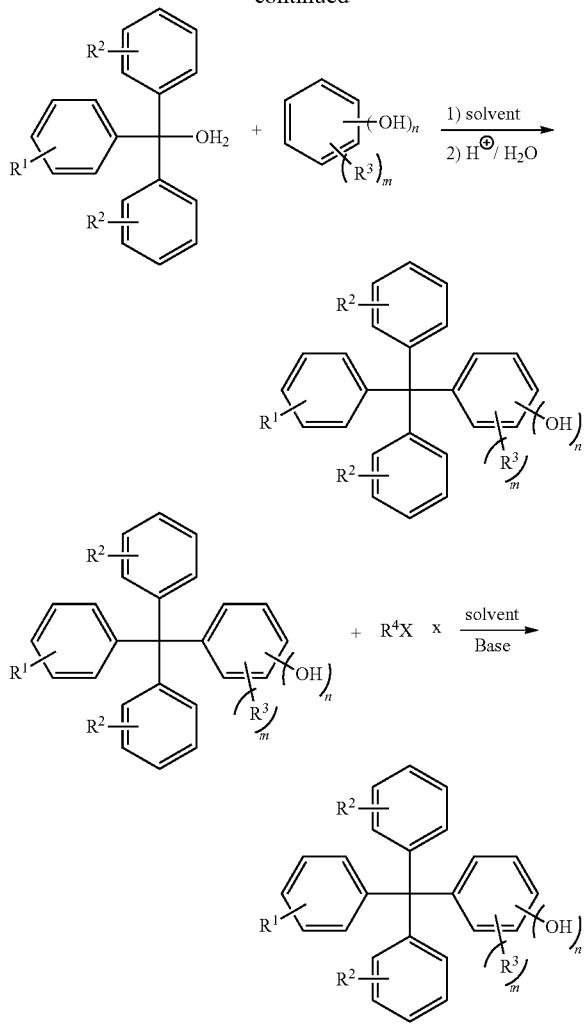

EXAMPLES

Common laboratory reagents and solvents were obtained from Sigma-Aldrich, Fluka, VWR, Acros, or Fisher Scientific, and were used as received. The benzoic acid esters, Grignard reagents and the phenols were obtained from Sigma-Aldrich.

Analysis Procedures

IR Analyses: IR analyses were performed using a Nicolet 560 FTIR spectrometer. For liquid samples, a small drop was cast as a neat film between two KBr plates. The IR spectrum was acquired in the transmission mode from 4000 to 400 $cm^{-1}$, with a spectral resolution of 4 $cm^{-1}$. A Happ-Genzel type apodization function was used.

NMR Analyses: Both $^1H$ and $^{13}C$ NMR spectra were acquired using a Bruker 200 NMR spectrometer operating at 4.7 T. $^1H$ spectra were obtained using an 8.2 second accumulation time and 2.0 KHz sweep width; the $^{13}C$ spectra were obtained at a 4.7 second accumulation time and 7.0 KHz sweep width. Methanol-$d_4$ was typically used as the solvent. Chemical shifts were referenced using the solvent resonances at 3.30 ppm for $^1H$, and at 59.05 ppm for $^{13}C$.

GPC ANALYSES: GPC analyses to follow the progress of synthesis reactions and to determine product purity were performed using a PerkinElmer Series 200 HPLC. Two Polymer Laboratories pLgel columns were used in series: 1) 300 mm×7.5 mm, 3 μ, 100 Å; 2) 300 mm×7.5 mm, 5 μ, 50 Å. These two columns are preceded by a guard column. The columns are maintained at 35° C. The mobile phase is 100% THF at a flow rate of 2 mL/minute. UV detection is at 270 nm. The program run time is 10 minutes.

GC ANALYSES: GC analyses to follow the progress of synthesis reactions and to determine product purity were performed using a Hewlett Packard Model 6890N gas chromatograph with FID detector. The column was a Thermo Scientific TR5, 7 meter×0.32 mm×0.25 μm film. The run program started with the oven at 50° C. with an initial hold time of 1 minute, followed by a temperature ramp up to 280° C. at 10° C./minute, and a final hold time of 20 minutes. The injection port temperature and detector temperatures were both 275° C. The sample injection size was 1 μL, and the carrier gas was helium at 1 mL/minute.

Melting Points: Melting points were determined using a Mel-Temp apparatus, and were uncorrected.

Synthesis of Alkyl Trityl Alcohols

General Synthesis Procedure: The following example is representative of the procedure used for the synthesis of all of the alkyl trityl alcohols. Synthesis data are summarized in Table 1 below.

Phenyldi-m-tolylmethanol [95938-57-1] (mmMTritOH): A 500 mL 4-neck flask was equipped with a magnetic stir bar, a 60 mL addition funnel, and 4 glass stoppers. The equipment was dried overnight in a 125° C. oven. Upon removal from the oven, the equipment was quickly assembled and was cooled to room temperature under a stream of nitrogen. The flask was charged with 200 mL of 1.0 M m-tolyl magnesium chloride in THF (0.2 moles). The addition funnel was charged with 13.63 grams (0.1 mole) of methyl benzoate in 30 mL of dry THF. Under a nitrogen blanket, the methyl benzoate solution was added to the stirred Grignard solution dropwise over a period of about 2.5 hours. During the addition, the Grignard solution turned from a yellow-brown to a violet color. Shortly after the addition began, an exotherm to about 37° C. was observed. The addition rate was adjusted to keep the reaction mixture temperature at or below this temperature. After the addition was completed, the reaction mixture temperature was increased to 60° C. for 2.5 hours. The reaction mixture was then stirred at room temperature for several days. GC analysis of a sample of the reaction mixture showed the presence of unreacted benzoate ester. The reaction mixture was re-heated to 60-65° C., monitoring the formation of product by GC analysis. After about 10 hours, the amount of unreacted ester was slightly more than 2 area %, and the amount of mmMTritOH was >85 area %. The reaction mixture was poured onto a mixture of 100 mL of 10 volume % sulfuric acid in water and about 300 grams of ice. About 100 mL of ether was added, and the mixture was stirred until the ice melted. The mixture was transferred to a separatory funnel, and the layers were separated. The aqueous layer was extracted with 1×50 mL of ether, and the ether layers were combined. The combined ether layers were washed with 2×50 mL of saturated aqueous sodium bicarbonate solution and then with 2×50 mL of saturated aqueous sodium chloride solution. The ether solution was dried over anhydrous magnesium sulfate, then it was filtered and the solvent was removed by rotary evaporation to give 26.33 grams of mmMTritOH as a viscous amber oil. Yield=91.3%. Product purity by GC analysis was >91 area %. Product structure was confined by IR, $^1H$— and $^{13}C$-NMR, and GC/MS analyses.

Synthesis of Alkyl Trityl Phenols

General Synthesis Procedure: The following example is representative of the procedure used for the synthesis of all of the alkyl trityl phenols. Synthesis data are summarized in Table 2 below.

2-(sec-Butyl)-4-(diphenyl)(p-tolyl)methyl)phenol (pMS4): A 100 mL 3-neck flask was equipped with a magnetic stirrer and a reflux condenser with nitrogen blanket. The flask was charged with 6.86 grams (0.025 moles) of diphenyl(p-tolyl)methanol (pMTritOH; [5440-76-6]), with 3.76 grams (0.025 moles) of o-sec-butylphenol, and with 50 mL of glacial acetic acid. The mixture was stirred under nitrogen at room temperature to give a clear yellow solution. To this solution were added 5 mL of concentrated sulfuric acid. The clear yellow acetic acid solution immediately turned deep red brown. The reaction mixture was stirred at room temperature, monitoring reaction progress by GPC analysis. After 6 days, the amount of remaining unreacted o-sec-butylphenol had decreased to about 7 area %, and the amount of mMS4 present had increased to about 83 area %. The reaction mixture was poured into about 250 mL of water and about 150 mL of toluene were added. The mixture was stirred at room temperature for about 1 hour, then the mixture was transferred to a separatory funnel. The layers were separated, and the aqueous layer was extracted with 1 x 50 mL of toluene, and the toluene layers were combined. The toluene solution was washed with 1×100 mL of water, and with 1×100 mL of saturated aqueous sodium chloride solution. The toluene solution was dried over anhydrous magnesium sulfate, then it was filtered and the solvent was removed by rotary evaporation to give 10 grams of pMS4 as a viscous dark red oil. Yield was 100%; product purity by GPC analysis was 82 area %. Product structure was confirmed by IR, $^1$H— and $^{13}$C-NMR, and GC/MS analyses.

Synthesis of Alkyl Trityl Phenyl Ethers

General Synthesis Procedure: The following example is representative of the procedure used for the synthesis of all of the alkyl trityl phenyl ethers. Synthesis data are summarized in Table 3 below.

((3,4-Bis(hexyloxy)phenyl)(p-tolyl)methylene)dibenzene (pM3,4-6): A 100 mL 3-neck flask was equipped with a magnetic stirrer, a reflux condenser with nitrogen blanket, and a heating mantle with a temperature controller and a thermocouple. The flask was charged with 3.67 grams (0.01 mole) of 4-(diphenyl(p-tolyl)methyl)benzene-1,2-diol (pM3,4), 1.41 grams (0.21 moles) of 85% potassium hydroxide pellets, and with 25 mL of dimethyl sulfoxide. The mixture was stirred under nitrogen and was heated to 105° C. Heating and stirring were continued until all of the potassium hydroxide pellets were dissolved. A dark red brown solution was obtained. The reaction mixture was cooled to 55° C., and 3.30 grams (0.02 moles) of bromohexane were added in one portion. As exotherm to 66° C. was observed. The reaction mixture was then maintained at 65° C. and was monitored by GC analysis. After 2 hours, almost no pM3,4 remained. The reaction mixture was poured into about 250 mL of water containing a few pellets of potassium hydroxide and several grams of sodium chloride. About 150 mL of toluene were added, and the mixture was stirred at room temperature for about 1 hour. The mixture was transferred to a separatory funnel and the layers were separated. The aqueous layer was extracted with 1×50 mL of toluene, and the toluene layers were combined. The toluene solution was washed with 1×75 mL of saturated aqueous sodium chloride solution, and was then dried over anhydrous magnesium sulfate. The solvent was removed by rotary evaporation to give 3.80 grams of pM3,4-6 as a dark red oil. Yield was 71%. Purity was >90 area % by GC. Product structure was confirmed by IR, $^1$H— and $^{13}$C-NMR, and GC/MS analyses.

Candidate Assessment Studies

GC/MS Studies: Stock solutions of alkyl trityl phenyl ether candidate were prepared in dichloromethane (DCM). These DCM solutions were used to establish GC retention times and MS fragmentation patterns. A summary of GC retention times and MS fragmentation data are summarized in Table 4 below.

GC/MS Parameters:
Column: Agilent DB 35 m, 15.0 m×0.25 mm×0.25 μ
Flow Rate: 1.5 mL/min He carrier gas
Oven: initial: 100° C.
Ramp 1: 20° C./min to 280° C.; Hold: 10 min.
Ramp 2: 20° C./min to 340° C.; Hold: 6 min
Inlet Temp.: 280° C.
Insert: Splitless; Vent: 15 min , Single taper, glass wool, deactivated, 5062-3587
Injection Volume: 3 μL; Viscosity: 5 sec., Plunger: fast
Mass Transfer Line Temp.: 280° C.
MS Quad: 200° C.; MS Source: 250° C.
Solvent Delay: 18.5 min Solubility Studies: The solubility properties of the alkyl trityl phenyl ethers were determined by mixing 0.1 grams of test sample with 0.9 grams of solvent. The mixtures were warmed to 60° C. for a few minutes to make homogeneous solutions. The solutions were cooled back to room temperature, and then they were placed into a freezer at −10° C. The solutions were checked daily to see if crystallization had occurred. The solvents evaluated were ADVASOL 200H (mixed aromatics solvent from Advanced Aromatics), ADVASOL 200H ND (naphthalene-depleted mixed aromatics solvent from Advanced Aromatics), cyclohexanone, and o-sec-butyl phenol (OSBP). Solubility data results are summarized in Table 5 below.

Assessment Summary: The GC retention time, GC/MS fragmentation and solubility performance results of the alkyl trityl phenyl ethers were all favorable for application as fuel markers.

TABLE 1

Synthesis Data for Alkyl Trityl Alcohols

| STRUCTURE | Designation | M.W. | % Yield | GC Area % Purity | mp, ° C. |
|---|---|---|---|---|---|
| 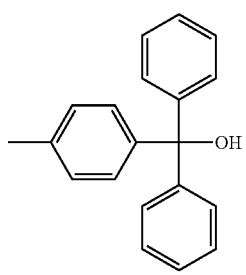 [SMILES: Cc1ccc(C(O)(c2ccccc2)c2ccccc2)cc1] | pMTritOH | 274.36 | 92.2 | 96.4 | 78-79 |

TABLE 1-continued

Synthesis Data for Alkyl Trityl Alcohols

| STRUCTURE | Designation | M.W. | % Yield | GC Area % Purity | mp, ° C. |
|---|---|---|---|---|---|
| 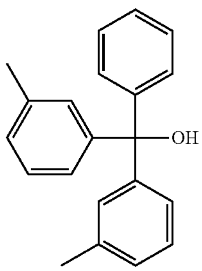 [SMILES: Cc1cccc(C(O)(c2ccccc2)c2cccc(C)c2)c1] | mmMTritOH | 288.38 | 90 | >91 | oil |
| 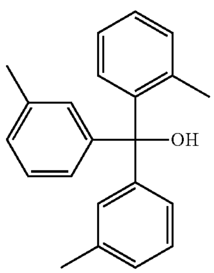 [SMILES: Cc1cccc(C(O)(c2cccc(C)c2)c2ccccc2C)c1] | ommMTritOH | 302.41 | 88.5 | >51 | oil |

TABLE 2

Synthesis Data for Alkyl Trityl Phenols

| STRUCTURE | Designation | M.W. | % yield | GPC (GC) Area % Purity | mp, ° C. |
|---|---|---|---|---|---|
| 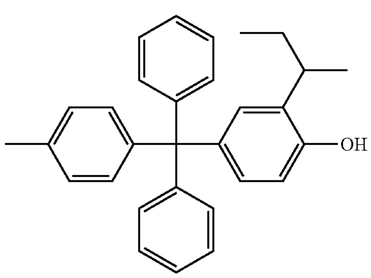 [SMILES: CCC(C)c1cc(C(c2ccccc2)(c2ccccc2)c2ccc(C)cc2)ccc1O] | pMS4 | 406.56 | 100 | 82 | oil |
| 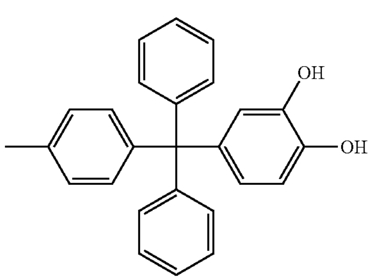 [SMILES: Cc1ccc(C(c2ccccc2)(c2ccccc2)c2ccc(O)c(O)c2)cc1] | pM3,4 | 366.45 | 55 | 89 | 175-180 |

TABLE 2-continued

Synthesis Data for Alkyl Trityl Phenols

| STRUCTURE | Designation | M.W. | % yield | GPC (GC) Area % Purity | mp, ° C. |
|---|---|---|---|---|---|
| 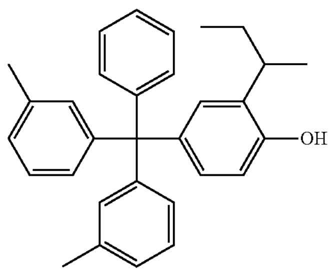 [SMILES: CCC(C)c1cc(C(c2ccccc2)(c2cccc(C)c2)c2cccc(C)c2)ccc1O] | mmMS4 | 420.59 | 78 | (75) | oil |

TABLE 3

Synthesis Data for Alkyl Trityl Phenyl Ethers

| STRUCTURE | Designation | M.W. | % yield | GPC (GC) Area % Purity | mp, ° C. |
|---|---|---|---|---|---|
| 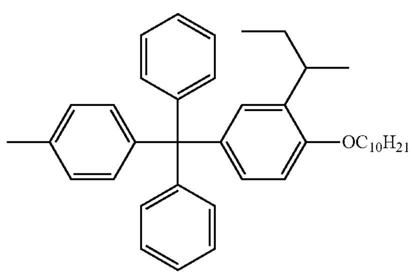 | pMS4-10 | 546.82 | 89 | (>75) | oil |
| 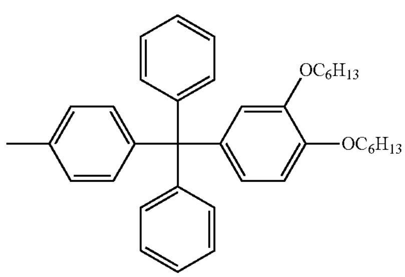 | pM3,4-6 | 534.77 | 71 | >90 | oil |
| 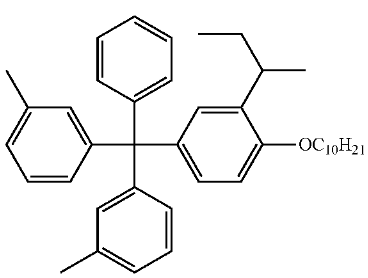 | mmMS4-10 | 560.40 | 79.6 | (70) | oil |

TABLE 4

Summary of GC Retention Time and GC/MS Fragmentation Data for Alkyl Trityl Phenyl Ethers

| STRUCTURE | DESIGNATION | M.W. | GC Retention Time, Min. | GC/MS Major Ion Masses, m/e |
|---|---|---|---|---|
| 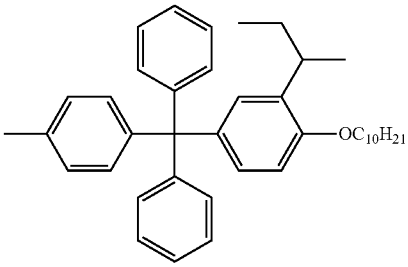 | pMS4-10 | 546.82 | 22.24 | 546, 469 |
| 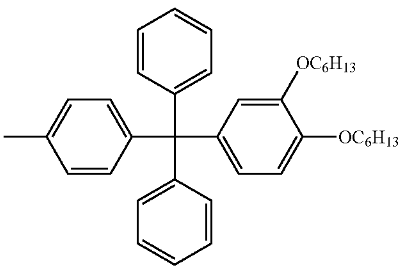 | pM3,4-6 | 534.77 | 22.89 | 534, 457, 373 |
| 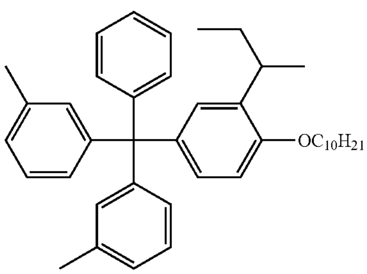 | mmMS4-10 | 560.40 | 21.69 | 560, 469 |

TABLE 5

Solubility Data Summary for Alkyl Trityl Phenyl Ethers

| Alkyl Trityl Phenyl Ether | WT. % Alkyl Trityl Phenyl Ether | SOLVENT SYSTEM | Solubility at −10° C., Days |
|---|---|---|---|
| pMS4-10 | 10 | 200H - OSBP (75:25, w:w) | Soluble after 7 days |
|  |  | 200H ND - OSBP (75:25, w:w) | Soluble after 7 days |
|  |  | 200H | Soluble after 7 days |
|  |  | 200H ND | Soluble after 7 days |
|  |  | 200H - cyclohexanone (75:25, w:w) | Soluble after 7 days |
|  |  | 200H ND - cyclohexanone (75:25, w:w) | Soluble after 7 days |
| pM3,4-6 | 10 | 200H - OSBP (75:25, w:w) | Soluble after 76 days |
|  |  | 200H ND - OSBP (75:25, w:w) | Soluble after 76 days |
|  |  | 200H | Soluble after 18 days; crystals after 35 days |
|  |  | 200H ND | Soluble after 18 days; crystals after 35 days |
|  |  | 200H - cyclohexanone (75:25, w:w) | Soluble after 7 days |
|  |  | 200H ND - cyclohexanone (75:25, w:w) | Soluble after 7 days |
| mmMS4-10 | 10 | 200H - OSBP (75:25, w:w) | Soluble after 102 days |
|  |  | 200H - cyclohexanone (75:25, w:w) | Soluble after 102 days |

The invention claimed is:
1. A compound having formula (I)

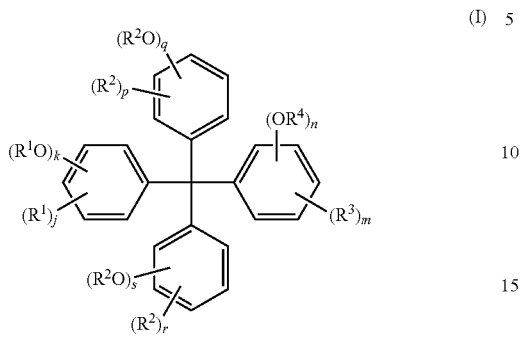

wherein $R^1$ and $R^2$ independently represent $C_1$-$C_6$ alkyl; $R^3$ is $C_2$-$C_6$ alkyl; $R^4$ is $C_1$-$C_{18}$ alkyl or $C_4$-$C_{18}$ heteroalkyl; m is one or two; n is one, two or three; and j, k, p, q, r and s independently are zero, one or two; provided that at least one of j, k, p, q, r and s is not zero.

2. The compound of claim 1 in which n is one or two; m is one; j, p and r are zero or one; and k, q and s are zero.

3. The compound of claim 2 in which $R^4$ is $C_2$-$C_{12}$ saturated alkyl.

4. The compound of claim 3 in which $R^1$ and $R^2$ independently represent $C_1$-$C_4$ alkyl.

5. The compound of claim 4 in which $R^3$ is $C_3$-$C_6$ alkyl.

6. The compound of claim 1 in which $R^3$ is $C_3$-$C_6$ alkyl.

* * * * *